United States Patent [19]

Nikles

[11] 4,311,820
[45] Jan. 19, 1982

[54] HOMOPOLYMERS AND COPOLYMERS OF VINYL ETHERS OF POLYALKYLPIPERIDINOLS AND THEIR USE AS STABILIZERS FOR PLASTICS

[75] Inventor: Erwin Nikles, Liestal, Switzerland

[73] Assignee: Ciba-Geigy Corporation, Ardsley, N.Y.

[21] Appl. No.: 118,356

[22] Filed: Feb. 4, 1980

[30] Foreign Application Priority Data

Feb. 14, 1979 [CH] Switzerland .................. 1465/79

[51] Int. Cl.$^3$ .............................................. C08F 16/14
[52] U.S. Cl. .................................... 526/265; 525/123; 525/203; 546/216; 546/221; 546/242
[58] Field of Search ........................................ 526/265

[56] References Cited

U.S. PATENT DOCUMENTS

| 3,640,928 | 2/1972 | Murayama et al. | 260/23 X A |
| 3,984,371 | 10/1976 | Murayama et al. | 260/45.75 C |
| 4,014,887 | 3/1977 | Randell et al. | 260/45.8 N |
| 4,046,737 | 9/1977 | Holt et al. | 260/45.8 N |

FOREIGN PATENT DOCUMENTS

| 496 | 2/1979 | European Pat. Off. |
| 2719131 | 12/1977 | Fed. Rep. of Germany |

OTHER PUBLICATIONS

W. Reppe, Annalen d. Chemie 601, 81–111 (1956).

Primary Examiner—Harry Wong, Jr.
Attorney, Agent, or Firm—Harry Falber

[57] ABSTRACT

Homopolymers and copolymers of vinyl ethers of the formula I

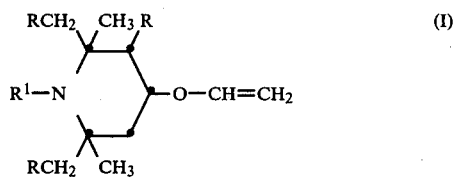

in which R is hydrogen or methyl and $R^1$ is hydrogen, $C_1$–$C_8$-alkyl, benzyl, allyl or $C_1$–$C_2$-acyl, are effective stabilizers for plastics, especially to protect them against photochemical degradation. The monomeric vinyl ethers of the formula I are novel compounds, which can be prepared from the corresponding piperidinols by vinylation by means of acetylene or by transvinylation by means of vinyl ethers or vinyl esters.

6 Claims, No Drawings

HOMOPOLYMERS AND COPOLYMERS OF VINYL ETHERS OF POLYALKYLPIPERIDINOLS AND THEIR USE AS STABILIZERS FOR PLASTICS

The invention relates to homopolymers and copolymers of 4-vinyloxypolyalkylpiperidines, which can be used as stabilisers for plastics, especially to protect them against damage by light. The invention also relates to the monomeric vinyl ethers on which the polymers are based and which can likewise be used as light stabilisers.

It is known that derivatives of polyalkylpiperidines, especially derivatives of 2,2,6,6-tetramethylpiperidine, are excellent light stabilisers for plastics. An example is bis-(2,2,6,6-tetramethyl-4-piperidyl) sebacate, which in particular is used industrially as a light stabiliser for polyolefins. Further esters and ethers of polyalkyl-4-piperidinols are described in German Offenlegungsschriften Nos. 1,929,928 and 2,258,752. For certain fields of application, the tendency to migration and the extractability of such low molecular weight piperidine derivatives are too high. This is the case in particular when the derivatives are used in thin layers, for example in films, coatings or fibres.

Therefore, higher molecular weight and especially polymeric derivatives of polyalkylpiperidines have already been proposed as light stabilisers for plastics, for example polycondensation products and polyaddition products have been proposed in German Offenlegungsschrift No. 2,719,131 or polymers of unsaturated esters and amides have been proposed in European Patent Application No. 78 100 360.3. A general problem with such polymeric light stabilisers is their compatibility with the plastics to be protected. In general, the capacity for migration and the extractability of the stabiliser do indeed fall as the molecular weight increases but, on the other hand, the compatibility of the stabiliser with the polymeric substrate also decreases. The compatibility is, however, dependent not only on the molecular weight of the stabiliser but also on its chemical structure and on the nature of the substrate.

It has been found that when vinyl ethers of polyalkyl-4-piperidinols are polymerised, products are formed which are readily compatible with many categories of plastics and display an excellent light-stabilising action with these, which action is retained even when the plastic is in use for a prolonged period. The properties of these polymers can be further modified by copolymerisation with other monomers, if the latter are capable of copolymerisation.

The invention therefore relates to homopolymers and copolymers of vinyl ethers of the formula I

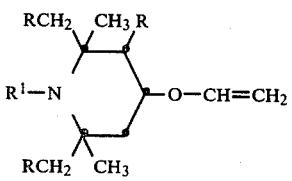
(I)

in which R is hydrogen or $CH_3$ and $R^1$ is hydrogen, $C_1$–$C_8$-alkyl, benzyl, allyl, formyl or acetyl. Preferably, R is hydrogen.

Alkyl $R^1$ can be, for example, methyl, ethyl, propyl, butyl, isoamyl, hexyl, n-octyl or iso-octyl; preferably, $R^1$ is methyl.

Preferred homopolymers and copolymers of vinyl ethers of the formula I are those in which $R^1$ is methyl and in which R is hydrogen.

The homopolymers of vinyl ethers of the formula I are also preferred, especially the homopolymers of 1,2,2,6,6-pentamethyl-4-piperidyl vinyl ether.

The homopolymerisation of the vinyl ethers of the formula I can be effected by the methods generally known for vinyl ethers, such as are described, for example, in Houben-Weyl, Methoden der Organischen Chemie (Methods of Organic Chemistry), Volume 14/1, pages 927–956. These methods include both free radical polymerisation and also metal-organic or cationic polymerisation. Free radical polymerisation is initiated by irradiation with UV light or by catalysts which form free radicals, for example peroxy compounds, and results only in polymers of low molecular weight. Polymerisation with metal-organic mixed catalysts, for example those of aluminum-alkyls and titanium halides, enables stereospecific polymers to be prepared. Cationic polymerisation of the vinyl ethers, which is initiated by electrophilic catalysts, for example boron fluoride, phosphorus pentafluoride, aluminium chloride or tin tetrachloride, is of particular importance. Boron fluoride and its EDA complexes, for example $BF_3$ etherates or $BF_3$-amine complexes, are particularly effective initiators for the polymerisation of the compounds of the formula I.

Independently of the initiator system chosen, the polymerisation can be effected in bulk, in solution or in dispersion or emulsion; in the main, the polymerisation is carried out in solution or in bulk.

The polymerisation proceeds at an adequate rate at room temperature or even at temperatures below room temperature (down to $-30°$ C.). In individual cases, for example in the case of high dilution, it can, however, be appropriate to accelerate the polymerisation by warming. The molecular weight of the polymers can be regulated by the amount of initiator, by the rate at which the initiator is added or by the addition of a regulator or of a chain stopper.

The homopolymers, according to the invention, of the vinyl ethers of the formula I in general have an average molecular weight of about 600 to 100,000, which corresponds approximately to a degree of polymerisation of 3 to 500. For use as stabilisers in plastics, polymers with an average molecular weight of about 3,000 to 50,000 are in particular of interest, since in this range not only a good stability to migration and stability to extraction but also an adequate compatibility in the substrate are ensured.

As already mentioned, the properties of these polymeric stabilisers can be modified by copolymerisation with a comonomer capable of copolymerisation. Suitable comonomers are, in particular, ethylenically unsaturated compounds, such as alkyl vinyl ethers, for example methyl vinyl ether or isobutyl vinyl ether; vinyl esters, for example vinyl acetate or vinyl propionate; other vinyl compounds, for example styrene, N-vinylpyrrolidone, vinyl chloride or vinylidene chloride; and derivatives of acrylic or methacrylic acid, for example methyl acrylate, tert.-butyl acrylate, methyl methacrylate, acrylamide, N-butyl methacrylamide, acrylonitrile or methacrylonitrile, and also maleic acid derivatives, such as esters, amides and cyclic imides of maleic acid. Preferred copolymers are those in which the comonomer is a vinyl ether having not more than 20 C. atoms.

The amount of comonomer can be up to 90 mol %. Higher proportions of comonomer are also possible, but the effectiveness of the copolymers as light stabilisers decreases as the comonomer content increases. Therefore, copolymers with a comonomer content of up to 50 mol % are preferred.

The copolymers can be statistical copolymers, block copolymers or alternating copolymers. Which of these structures is predominantly formed depends on the nature of the initiator used and of the comonomer used and on the sequence of the addition and other process measures. Cationic initiators are suitable for the copolymerisation with other vinyl ethers; the copolymerisation with other unsaturated compounds can be initiated either cationically or by free radicals. In general, the rules which are generally known for the copolymerisation of vinyl ethers and are described, for example, in Houben-Weyl, Methoden der Organischen Chemie (Methods of Organic Chemistry), 14/1, 956–972 also apply in the case of the copolymerisation of vinyl ethers of the formula I.

The monomeric vinyl ethers of the formula I are novel compounds which are also a subject of the invention. They can be prepared by the methods generally known for the preparation of vinyl ethers. These include, in particular, preparation by adding acetylene onto polyalkyl-4-piperidinols in the presence of catalysts, which can preferably be carried out under pressure (about 10–20 atmospheres). Suitable catalysts for this reaction are the same as those used for the vinylation of simple alcohols, such as have been described, for example, by W. Reppe in Ann. 601, 81 (1956). Examples are potassium hydroxide or sodium hydroxide.

Another process, which is particularly suitable as a laboratory method, is the transvinylation of polyalkyl-4-piperidinols with vinyl esters, for example vinyl acetate, or with vinyl ethers, for example isobutyl vinyl ether. In both cases the reaction is carried out in the presence of heavy metal catalysts, for example mercury salts, and with an excess of vinylating agents.

Other methods for the preparation of the vinyl ethers according to the invention are the reaction of alkali metal salts of polyalkyl-4-piperidinols with vinyl chloride or the pyrolysis of acetals of polyalkyl-4-piperidinols.

The vinyl ethers of the formula I are liquid or low-melting compounds which can be purified by distillation. They are readily soluble in most organic solvents; in water their solubility is low.

The vinyl ethers of the formula I also act as light stabilisers and can be used as such. However, their significance as monomeric starting materials for the homopolymers and copolymers described above is more important.

Examples of vinyl ethers of the formula I which are suitable for homopolymerisation and copolymerisation are: 2,2,6,6-tetramethyl-4-piperidyl vinyl ether, 1,2,2,6,6-pentamethyl-4-piperidyl vinyl ether, 2,3,6-trimethyl-2,6-diethyl-4-piperidyl vinyl ether, 1-propyl-2,2,6,6-tetramethyl-4-piperidyl vinyl ether, 1-isobutyl-2,2,6,6-tetramethyl-4-piperidyl vinyl ether, 1-hexyl-2,2,6,6-tetramethyl-4-piperidyl vinyl ether, 1-octyl-2,2,6,6-tetramethyl-4-piperidyl vinyl ether, 1-benzyl-2,2,6,6-tetramethyl-4-piperidyl vinyl ether, 1-allyl-2,2,6,6-tetramethyl-4-piperidyl vinyl ether and 1-ben-zyl-2,2,6,6-tetramethyl-4-piperidyl vinyl ether.

The homopolymers and copolymers of vinyl ethers of the formula I can be used according to the invention as stabilisers for plastics to protect them against thermoxidative degradation and preferably against photochemical degradation. Plastics which can be used are in particular those which are sensitive to the action of light and are listed, for example, in German Offenlegungsschrift No. 2,647,452 on pages 12–14.

The stabilisation of polyolefins, styrene polymers and polyurethanes is of particular importance. Examples of such polymers are high density and low density polyethylene, polypropylene, ethylene/propylene copolymers, polystyrene, styrene/butadiene/acrylonitrile copolymers, mixtures of polyolefins or of styrene polymers and polyurethanes based on polyethers of polyesters, in the form of lacquers, fibres, elastomers or foams.

The polyvinyl ethers according to the invention are particularly suitable for the light stabilisation of polypropylene multifilaments which have been latexed and treated at elevated temperature (for example 120° C.).

The stabilisers according to the invention are added to the plastics in a concentration of 0.01 to 5% by weight, based on the material to be stabilised. Preferably, 0.1 to 2% by weight of the compounds, based on the material to be stabilised, are incorporated into the latter.

Incorporation can be effected after polymerisation, for example by mixing the compounds and, if desired, further additives into the melt by the methods customary in industry, before or during shaping, or also by applying the dissolved or dispersed compounds to the polymer, with subsequent evaporation of the solvent if necessary.

The stabilisers can also be added to the plastics to be stabilised, in the form of a master batch which contains these compounds, for example in a concentration of 2.5 to 25% by weight.

In the case of crosslinked polyethylene, the compounds are added prior to crosslinking.

In addition to the polymeric stabilisers, yet further known stabilisers can also be added to the plastics. These can be, for example, antioxidants, light stabilisers or metal deactivators, or also co-stabilisers, for example those of the phosphite type.

Furthermore, other additives customary in plastics technology, for example flameproofing agents, antistatic agents, plasticisers, lubricants, blowing agents, pigments, reinforcing materials or fillers, can be added.

When known stabilisers are also used, synergistic effects can arise and this is frequently the case when other light stabilisers or organic phosphites are additionally used.

The invention therefore also relates to the plastics stabilised by the addition of 0.01 to 5% by weight of a homopolymer or copolymer of a vinyl ether of the formula I, which plastics can, if desired, contain yet further known and conventional additives. The plastics stabilised in this way can be used in very diverse forms, for example in the form of films, fibres, tapes or profiles or as binders for lacquers, adhesives or putties.

The preparation and use of the compounds according to the invention is described in more detail in the following examples. Parts and percentages are by weight. The temperatures are given in degrees centigrade.

EXAMPLE 1

1,2,2,6,6-Pentamethyl-4-piperidyl vinyl ether 2 g of mercury acetate were added to a mixture of 28 g of 1,2,2,6,6-pentamethyl-4-piperidinol and 164 g of butyl vinyl ether and the mixture was boiled under reflux. After 11 hours the conversion of the alcohol employed determined by gas chromatography was about 77%. The batch was poured into 600 ml of water and diluted with hexane. The organic phase was separated off and dried over anhydrous sodium sulfate. The solvent and the excess butyl vinyl ether were recovered by distillation. The residue was distilled under 15 mm Hg and 20 g of 1,2,2,6,6-pentamethyl-4-piperidyl vinyl ether with a boiling point of 98° were obtained.

It was also possible to obtain the same product by reacting 1,2,2,6,6-pentamethyl-4-piperidinol with acetylene at 170° and under 15 atmospheres pressure in the presence of 2 g of potassium hydroxide.

1-n-Octyl-2,2,6,6-tetramethyl-4-piperidyl vinyl ether was also prepared by a procedure analogous to that described above. (Purification by molecular distillation at 100°/0.01 mm Hg.).

EXAMPLE 2

1-Benzyl-2,2,6,6-tetramethyl-4-piperidyl vinyl ether

A mixture of 123.6 g of 1-benzyl-2,2,6,6-tetramethyl-4-piperidinol and 4 g of potassium hydroxide was dehydrated by azeotropic distillation with toluene. The toluene was evaporated off and the residue was dried under 0.01 mm Hg at 40°. This mixture was then stirred at 170°-180° and under 15 atmospheres pressure in an acetylene atmosphere until no further acetylene was taken up (5 hours). The product was distilled. Boiling point 116°/0.5 mm Hg. Yield 106 g.

The following compounds were obtained in a similar manner: 2,3,6-trimethyl-2,6-diethyl-4-piperidyl vinyl ether, boiling point 121°/18 mm Hg; 1-allyl-2,2,6,6-tetramethyl-4-piperidyl vinyl ether, boiling point 63°/0.1 mm Hg; 1-butyl-2,2,6,6-tetramethyl-4-piperidyl vinyl ether, boiling point 66°-67°/0.1 mm Hg and 2,2,6,6-tetramethyl-4-piperidyl vinyl ether, boiling point 78°/19 mm Hg.

EXAMPLE 3

1-Acetyl-2,2,6,6-tetramethyl-4-piperidyl vinyl ether 40 g of 2,2,6,6-tetramethyl-4-piperidyl vinyl ether were dissolved in 270 ml of dry pyridine and 200 ml of acetic anhydride were added. The mixture was warmed slowly and finally was refluxed for 36 hours. The volatile constituents were evaporated off under a water pump vacuum on a boiling water bath and the residue was distilled under a high vacuum. Boiling point 88°/0.1 mm Hg.

EXAMPLE 4

Poly-(1,2,2,6,6-pentamethyl-4-piperidyl vinyl ether)

(a) 4 ml of boron trifluoride-ethyl-etherate, dissolved in 4 ml of dry ether, were added dropwise in the course of 3 hours, at −20°, to 50 g of 1,2,2,6,6-pentamethyl-4-piperidyl vinyl ether. The mixture was left to stand for about 20 hours at −18°. The product was precipitated by diluting with acetonitrile and dissolved in hexane, the hexane solution was washed with dilute sodium carbonate solution and the product was re-precipitated by adding acetonitrile. Melting point 128°-134°. Average molecular weight $\overline{M}n$: 27,000.

(b) 100 g of 1,2,2,6,6-pentamethyl-4-piperidyl vinyl ether were dissolved in 100 ml of dry hexane and 15 ml of boron trifluoride-ethyl-etherate, dissolved in 30 ml of dry ether, were added in the course of 6 hours. The solution, which became highly viscous, was diluted with 50 ml of hexane 3 hours after the start of the reaction and after a further 3½ hours was diluted with 100 ml of methylene chloride. After a total of 9½ hours, the mixture was diluted with 500 ml of methylene chloride, washed with four times 100 ml of 2 N sodium carbonate solution and then with water, dried over anhydrous sodium sulfate and filtered and the filtrate was evaporated. The liquid residue was ground in the presence of a total of 2 l of acetonitrile. The product, which separates out as a solid, was filtered off and dried. 88 g of poly-(1,2,2,6,6-pentamethyl-4-piperidyl vinyl ether) with a melting point of 107°-128° were obtained; $\overline{M}n$ 5,900.

The following compounds were prepared analogously: poly-(1-allyl-2,2,6,6-tetramethyl-4-piperidyl vinyl ether), melting point 122°-138°, $\overline{M}n$: 27,400; poly-(1-butyl-2,2,6,6-tetramethyl-4-piperidyl vinyl ether), melting point 110°-168°, $\overline{M}n$: about 3,000-4,000, and poly-(1-acetyl-2,2,6,6-tetramethyl-4-piperidyl vinyl ether) (polymerisation in methylene chloride at −20° for 3 days).

EXAMPLE 5

Poly-(1-benzyl-2,2,6,6-tetramethyl-4-piperidyl vinyl ether)

5 g of 1-benzyl-2,2,6,6-tetramethyl-4-piperidyl vinyl ether were dissolved in 50 ml of dry toluene, and 0.3 ml of boron trifluoride-ethyl-etherate dissolved in 10 ml of toluene was added. After standing at room temperature for 20 hours, the solution was highly viscous. The mixture was diluted with 50 ml of methylene chloride, washed with sodium carbonate solution, dried over anhydrous sodium sulfate and evaporated. The residue, which was a hard resin, was dissolved in methyl ethyl ketone and precipitated with methanol. 4.2 g of polymer with a melting range of 110°-210° and an average molecular weight Mn of 60,300 were obtained.

EXAMPLE 6

Copolymerisation of 1,2,2,6,6-pentamethyl-4-piperidyl vinyl ether with isobutyl vinyl ether 15 g of 1,2,2,6,6-pentamethyl-4-piperidyl vinyl ether and 7.6 g of isobutyl vinyl ether were dissolved in 20 ml of hexane, and 1.2 ml of boron trifluoride-ethyl-etherate dissolved in 10 ml of dry ether were added dropwise at −20° in the course of 5 hours. After about 20 hours at about −20°, the mixture was diluted with methylene chloride, washed with dilute sodium carbonate solution and water, dried and filtered and the filtrate was evaporated. The residual resin was ground with 300 ml of acetonitrile and left to stand for 14 hours. The solid product formed was filtered off and dried. Melting point 72°-83°, Mn: 7,300, nitrogen content: 5.25%.

In an analogous manner, 5 g of 1,2,2,6,6-pentamethyl-4-piperidyl vinyl ether and 1.83 g of ethyl vinyl ether were copolymerised in 10 ml of hexane. The resulting copolymer melts at 86°-93° and has an average molecular weight $\overline{M}n$ of 6,300.

EXAMPLE 7

Copolymer of 1,2,2,6,6-pentamethyl-4-piperidyl vinyl ether and acrylonitrile 6 g of 1,2,2,6,6-pentamethyl-4-piperidyl vinyl ether and 6 g of acrylonitrile were dissolved in 10 ml of toluene, 0.2 g of azoisobutyronitrile was added and the mixture was left to stand for 14 days at room temperature. The mixture was diluted with methylene chloride, washed with water, dried and filtered and the filtrate was evaporated. The residue was precipitated from hexane at −20°. The resulting product softens above 100° and does not melt completely up to 260°. $\overline{M}n$ about 2,500, nitrogen content 14.5%.

EXAMPLE 8

Copolymer of 2,2,6,6-tetramethyl-4-piperidyl vinyl ether and N-butyl-maleimide

A solution of 4 g of 2,2,6,6-tetramethyl-4-piperidyl vinyl ether, 3.3 g of N-n-butyl-maleimide and 50 mg of azoisobutyronitrile in 40 ml of ligroin was kept at 50° for 24 hours under nitrogen. The solvent was evaporated off. The residue was treated with hexane and the solid product was filtered off and dried. Melting point ∼125°, Mn: 1,100, nitrogen content 7.9%.

EXAMPLE 9

Light stabilising action in polypropylene fibres 1,000 parts of polypropylene powder (melt index ∼18) which has not been stabilised are mixed in a high-speed mixer with 1 part of calcium stearate, 0.5 part of calcium bis-(4′-hydroxy-3′,5′-di-tertiary butyl-benzyl-ethylphosphonate), 2.5 parts of titanium dioxide and 3 parts of the light stabilisers listed in the table and the mixture is then extruded in an extruder at 220° C. and granulated. The resulting granules are spun in a laboratory melt-spinning installation at a maximum temperature of 270° C. and a speed of 600 m/minute to give a 403/37 denier multifilament. This is drawn and twisted using a draw-twister. The drawing ratio is 1:3.2, so that ultimately multifilaments of 130/37 denier are obtained. These multifilaments are mounted on white card, a further strip of card being attached at each end of the card, so that the filaments in the central part are stretched over 5 cm without contact. The fibres are exposed in a Xenotest 1200. The exposure time which elapses before there is a 50% loss in the tear strength is taken as a measure of the protective effect. The results are summarised in the table.

| Light stabiliser used | Exposure time which elapses before there is a 50% loss in the tear strength |
|---|---|
| none | 400 hours |
| 0.3% of poly-(1,2,2,6,6-pentamethyl-4-piperidyl vinyl ether) | 4,700 hours |
| 0.3% of poly-(1-allyl-2,2,6,6-tetramethyl-4-piperidyl vinyl ether) | 1,175 hours |

What is claimed is:

1. A homopolymer of a vinyl ether of the formula I

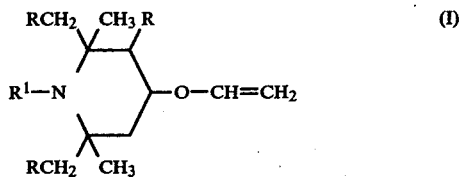

in which R is hydrogen or methyl and $R^1$ is hydrogen, $C_1$–$C_8$ alkyl, benzyl, allyl, formyl or acetyl; or a copolymer of said vinyl ether with up to 90 mol % of an ethylenically unsaturated comonomer.

2. A homopolymer or copolymer according to claim 1 of a vinyl ether of the formula I in which R is hydrogen.

3. A homopolymer or copolymer according to claim 1 of a vinyl ether of the formula I in which R is hydrogen and $R^1$ is methyl.

4. A homopolymer according to claim 1 of a vinyl ether of the formula I.

5. Poly-(1,2,2,6,6-pentamethyl-4-piperidyl vinyl ether).

6. A copolymer according to claim 1, in which the ethylenically unsaturated comonomer is a vinyl ether having not more than 20 C atoms.

* * * * *